(12) United States Patent
Velusamy et al.

(10) Patent No.: US 8,401,620 B2
(45) Date of Patent: Mar. 19, 2013

(54) NEEDLE POSITIONING APPARATUS AND METHOD

(75) Inventors: Gnanasekar Velusamy, TamilNadu (IN); Kannan Neelakanta Sarma, TamilNadu (IN); Kasi Viswanathan Agilandam, Karnataka (IN); Roy Santosham, TamilNadu (IN)

(73) Assignee: Perfint Healthcare Private Limited (IN)

( * ) Notice: Subject to any disclaimer, the term of this patent is extended or adjusted under 35 U.S.C. 154(b) by 954 days.

(21) Appl. No.: 11/682,375

(22) Filed: Mar. 6, 2007

(65) Prior Publication Data

US 2008/0091101 A1    Apr. 17, 2008

(30) Foreign Application Priority Data

Oct. 16, 2006   (IN) .......................... 1903/CHE/2006

(51) Int. Cl.
*A61B 5/055* (2006.01)
*A61B 19/00* (2006.01)

(52) U.S. Cl. .................. 600/427; 600/424; 606/130
(58) Field of Classification Search .................. None
See application file for complete search history.

(56) References Cited

U.S. PATENT DOCUMENTS

| | | |
|---|---|---|
| 4,583,538 A | 4/1986 | Onik et al. |
| 4,883,053 A | 11/1989 | Simon |
| 5,078,140 A * | 1/1992 | Kwoh .................. 600/417 |
| 5,201,742 A | 4/1993 | Hasson |
| 5,371,778 A | 12/1994 | Yanof et al. |
| 5,590,655 A | 1/1997 | Hussman |
| 5,628,327 A | 5/1997 | Unger et al. |
| 5,734,384 A | 3/1998 | Yanof et al. |
| 5,769,086 A | 6/1998 | Ritchart |
| 5,823,993 A | 10/1998 | Lemelson |
| 5,834,759 A | 11/1998 | Glossop |
| 5,957,933 A | 9/1999 | Yanof et al. |
| 6,021,342 A | 2/2000 | Brabrand |
| 6,035,228 A | 3/2000 | Yanof et al. |
| 6,052,611 A | 4/2000 | Yanof et al. |

(Continued)

FOREIGN PATENT DOCUMENTS

| | | |
|---|---|---|
| EP | 1524626 A2 | 4/2005 |
| EP | 1 791 070 A2 | 5/2007 |

(Continued)

OTHER PUBLICATIONS

Joachim Kettenbach, Robot-Assisted Biopsy Using Computed Tomography-Guidance, Investigative Radiology, Apr. 2005, p. 219, vol. 40, No. 4, Lippincott Williams & Wilkins, Philadelphia.

(Continued)

*Primary Examiner* — Long V. Le
*Assistant Examiner* — Angela M Hoffa

(57) ABSTRACT

Apparatus for accurate positioning of a needle guide is disclosed. The apparatus provides a means for taking as input the position vector for the point of insertion of the needle into the body. This point of insertion can be selected from images produced by a Computer Tomography system. Similarly, the apparatus has a means for taking as input the point of target. A controller determines the directional vector between point of insertion and point of target. A guide manipulator accurately positions the needle guide in line with the directional vector, such that the needle can easily be inserted through the guide to the point of target. The positioning of the guide manipulator in accordance with the directional vector is done with the help of motors.

26 Claims, 13 Drawing Sheets

U.S. PATENT DOCUMENTS

| | | | |
|---|---|---|---|
| 6,064,904 A | 5/2000 | Yanof et al. | |
| 6,097,994 A * | 8/2000 | Navab et al. | 700/245 |
| 6,110,112 A * | 8/2000 | Heywang-Koebrunner | 600/439 |
| 6,139,544 A | 10/2000 | Mikus et al. | |
| 6,149,592 A | 11/2000 | Yanof et al. | |
| 6,167,296 A | 12/2000 | Shahidi | |
| 6,176,835 B1 | 1/2001 | Pachal | |
| 6,185,445 B1 | 2/2001 | Knuttel | |
| 6,203,543 B1 | 3/2001 | Glossop | |
| 6,216,029 B1 * | 4/2001 | Paltieli | 600/427 |
| 6,245,028 B1 * | 6/2001 | Furst et al. | 600/568 |
| 6,246,898 B1 | 6/2001 | Vesely et al. | |
| 6,249,713 B1 | 6/2001 | Geiger et al. | |
| 6,317,616 B1 | 11/2001 | Glossop | |
| 6,334,067 B1 | 12/2001 | Brabrand | |
| 6,366,796 B1 | 4/2002 | Yanof et al. | |
| 6,442,417 B1 | 8/2002 | Shahidi et al. | |
| 6,443,960 B1 | 9/2002 | Brabrand et al. | |
| 6,468,226 B1 * | 10/2002 | McIntyre, IV | 600/564 |
| D466,609 S | 12/2002 | Glossop | |
| 6,505,065 B1 * | 1/2003 | Yanof et al. | 600/427 |
| 6,529,758 B2 | 3/2003 | Shahidi | |
| 6,546,279 B1 * | 4/2003 | Bova et al. | 600/429 |
| 6,575,969 B1 | 6/2003 | Rittman, III et al. | |
| 6,591,130 B2 | 7/2003 | Shahidi | |
| 6,665,554 B1 | 12/2003 | Charles | |
| 6,674,833 B2 | 1/2004 | Shahidi et al. | |
| 6,687,529 B2 | 2/2004 | Van Vaals | |
| 6,694,164 B2 | 2/2004 | Glossop | |
| 6,695,786 B2 | 2/2004 | Wang et al. | |
| 6,778,850 B1 | 8/2004 | Adler et al. | |
| 6,782,287 B2 | 8/2004 | Grzeszczuk et al. | |
| 6,785,571 B2 | 8/2004 | Glossop | |
| 6,785,572 B2 | 8/2004 | Yanof et al. | |
| 6,850,794 B2 | 2/2005 | Shahidi | |
| 6,853,856 B2 | 2/2005 | Yanof | |
| 6,889,073 B2 | 5/2005 | Lampman et al. | |
| 7,008,373 B2 | 3/2006 | Stoianovici et al. | |
| 7,182,083 B2 | 2/2007 | Yanof et al. | |
| 7,192,430 B2 | 3/2007 | Truckai et al. | |
| 7,225,012 B1 | 5/2007 | Susil et al. | |
| 7,245,958 B1 * | 7/2007 | Navab et al. | 600/407 |
| 7,322,990 B1 | 1/2008 | Mark et al. | |
| 7,333,644 B2 | 2/2008 | Jerebko et al. | |
| 7,398,116 B2 | 7/2008 | Edwards | |
| 7,440,793 B2 | 10/2008 | Chauhan et al. | |
| 7,466,303 B2 | 12/2008 | Yi et al. | |
| 7,660,623 B2 | 2/2010 | Hunter et al. | |
| 7,722,565 B2 | 5/2010 | Wood et al. | |
| 7,742,801 B2 | 6/2010 | Neubauer et al. | |
| 7,751,868 B2 | 7/2010 | Glossop | |
| 7,801,583 B2 | 9/2010 | Brabrand | |
| 7,805,269 B2 | 9/2010 | Glossop | |
| 7,822,466 B2 | 10/2010 | Stoianovici et al. | |
| 7,824,417 B2 | 11/2010 | Magnusson et al. | |
| 7,840,251 B2 | 11/2010 | Glossop | |
| 7,840,254 B2 | 11/2010 | Glossop | |
| 7,853,307 B2 | 12/2010 | Edwards | |
| 7,871,406 B2 | 1/2011 | Nields et al. | |
| 7,920,909 B2 | 4/2011 | Lyon et al. | |
| 7,962,193 B2 | 6/2011 | Edwards et al. | |
| 8,041,412 B2 | 10/2011 | Glossop et al. | |
| 8,150,495 B2 | 4/2012 | Edwards et al. | |
| 2001/0025183 A1 | 9/2001 | Shahidi | |
| 2001/0037064 A1 | 11/2001 | Shahidi | |
| 2002/0143317 A1 | 10/2002 | Glossop | |
| 2002/0156376 A1 * | 10/2002 | Wang et al. | 600/439 |
| 2003/0018251 A1 | 1/2003 | Solomon | |
| 2003/0032878 A1 | 2/2003 | Shahidi | |
| 2003/0097055 A1 | 5/2003 | Yanof et al. | |
| 2003/0171672 A1 | 9/2003 | Varghese et al. | |
| 2003/0171680 A1 | 9/2003 | Paltieli | |
| 2004/0010190 A1 | 1/2004 | Shahidi | |
| 2004/0152970 A1 | 8/2004 | Hunter et al. | |
| 2004/0167389 A1 | 8/2004 | Brabrand | |
| 2004/0176690 A1 | 9/2004 | Brabrand | |
| 2004/0220562 A1 | 11/2004 | Garabedian et al. | |
| 2005/0041843 A1 | 2/2005 | Sawyer | |
| 2005/0085793 A1 | 4/2005 | Glossop | |
| 2005/0177054 A1 | 8/2005 | Yi et al. | |
| 2005/0182319 A1 | 8/2005 | Glossop | |
| 2005/0184988 A1 | 8/2005 | Yanof et al. | |
| 2005/0267359 A1 | 12/2005 | Hussaini et al. | |
| 2006/0020279 A1 | 1/2006 | Chauhan et al. | |
| 2006/0052693 A1 | 3/2006 | Tynes | |
| 2006/0089624 A1 | 4/2006 | Voegele et al. | |
| 2006/0122497 A1 | 6/2006 | Glossop | |
| 2006/0149147 A1 * | 7/2006 | Yanof | 600/424 |
| 2006/0173269 A1 | 8/2006 | Glossop | |
| 2006/0173291 A1 | 8/2006 | Glossop | |
| 2006/0184016 A1 | 8/2006 | Glossop | |
| 2007/0016067 A1 * | 1/2007 | Webster et al. | 600/464 |
| 2007/0032723 A1 | 2/2007 | Glossop | |
| 2007/0049820 A1 * | 3/2007 | Stern et al. | 600/427 |
| 2007/0055128 A1 | 3/2007 | Glossop | |
| 2007/0060790 A1 | 3/2007 | Kura et al. | |
| 2007/0066881 A1 | 3/2007 | Edwards et al. | |
| 2007/0078334 A1 * | 4/2007 | Scully et al. | 600/424 |
| 2007/0167787 A1 | 7/2007 | Glossop et al. | |
| 2007/0167806 A1 | 7/2007 | Wood et al. | |
| 2007/0197896 A1 * | 8/2007 | Moll et al. | 600/407 |
| 2007/0232882 A1 | 10/2007 | Glossop et al. | |
| 2008/0004481 A1 | 1/2008 | Bax et al. | |
| 2008/0009791 A1 | 1/2008 | Cohen et al. | |
| 2008/0015677 A1 | 1/2008 | Glossop et al. | |
| 2008/0033417 A1 | 2/2008 | Nields et al. | |
| 2008/0033418 A1 | 2/2008 | Nields et al. | |
| 2008/0033419 A1 | 2/2008 | Nields et al. | |
| 2008/0033420 A1 | 2/2008 | Nields et al. | |
| 2008/0071215 A1 | 3/2008 | Woods et al. | |
| 2008/0125649 A1 | 5/2008 | Meyer et al. | |
| 2008/0132797 A1 | 6/2008 | Brabrand | |
| 2008/0281181 A1 | 11/2008 | Manzione et al. | |
| 2008/0298655 A1 | 12/2008 | Edwards | |
| 2008/0312561 A1 | 12/2008 | Chauhan | |
| 2009/0221999 A1 | 9/2009 | Shahidi | |
| 2009/0281566 A1 | 11/2009 | Edwards et al. | |
| 2010/0185087 A1 | 7/2010 | Nields et al. | |
| 2011/0054309 A1 | 3/2011 | Edwards | |
| 2011/0184276 A1 | 7/2011 | Lyon et al. | |
| 2011/0208044 A1 | 8/2011 | Edwards et al. | |
| 2012/0158047 A1 | 6/2012 | Edwards et al. | |

FOREIGN PATENT DOCUMENTS

| | | |
|---|---|---|
| EP | 1 534 153 B1 | 4/2009 |
| WO | WO 99/00052 A1 | 1/1999 |
| WO | WO 02/24051 A2 | 3/2002 |
| WO | WO 03/091839 A2 | 11/2003 |
| WO | WO 2004/086974 A1 | 10/2004 |

OTHER PUBLICATIONS

Barrett, S. et al., "A Remote Needle Guidance System for Percutaneous Biopsies," Proceedings of IDETC/CIE 2005, Sep. 2005, 9 pages.

Maurin, B. et al., "A Patient-Mounted Robotic Platform for CT-scan Guided Procedures," IEEE Transactions on Biomedical Engineering, published at least as early as Feb. 16, 2010, 8 pages.

McCreedy, E. et al., "Radio Frequency Ablation Registration, Segmentation, and Fusion Tool," IEEE Trans Inf Technol Biomed., Jul. 2006, vol. 10, No. 3, 16 pages.

Wood, B. et al., "CT-guided interventional oncology: bridging the gap between diagnosis and therapy," MedicaMundi, vol. 49, No. 3, Nov. 2005; 5 pages.

International Search Report and Written Opinion for PCT/IN08/00507, mailed on Mar. 23, 2009; 7 pages.

* cited by examiner

NEEDLE POSITIONING APPARATUS AND METHOD

CROSS-REFERENCE TO RELATED APPLICATIONS

The present invention claims the benefit of the filing date of Indian patent application number 1903/CHE/2006, filed 16 Oct. 2006, the text of which is included by reference herein.

FIELD OF INVENTION

The present invention relates to a needle guide positioner. In particular, the present invention relates to an apparatus and a method for accurately positioning a needle with respect to a target within a patient's body to facilitate different clinical procedures involving needle insertion into the patient's body.

BACKGROUND

Biopsy is a medical procedure in which cells or tissues are removed from the body for examination. The procedure involves removing specimens of a tissue from part of a body lesion. These specimens are then examined under the microscope to determine the medical condition.

In a typical biopsy procedure, the affected part of the patient's body is scanned to pinpoint the location of the lesion. In order to extract samples from the lesion, a needle is inserted to touch the lesion. The needle is inserted such that it does not puncture any other vital organ or structure in the patient's body. Currently, the biopsy incisions are usually made by hand. The practitioner determines the point of insertion of the biopsy needle through external measurements. For example, the point of insertion can be determined by placing a cotton pellet mixed with contrast or iodine. The area can also be determined by drawing lines on the patient or by marking the area of entry by a marker. The position and angle of the insertion in such cases may not be accurate resulting in repeated insertions in the patient's body.

Image guided interventional procedures are preferred by practitioners. Such procedure shows the path taken by the needle during insertion, thereby reducing the risk to the patients and increasing the accuracy of insertion. Also, image guidance helps to avoid unwanted injury to vital organs and blood vessels. Commonly used imaging systems are Ultrasound, X-Rays, C-Arms, Computed Tomography Scanners, Magnetic Resonance Imaging etc.

Information relevant to attempts to address the limitations inherent in existing methods of needle positioning can be found in US patents U.S. Pat. No. 6,785,572, and U.S. Pat. No. 6,246,898; US patent applications US2004152970A1, US2005177054A1, and US2006020279A1; European patent EPI 524626, and WIPO patent application WO03091839A2. However, each one of these references suffers from one or more of the following limitations. Firstly, these devices require real time imaging and tracking of the needle. Therefore, the radiation exposure time to the patient and practitioner is high. Secondly, the cost of such devices as well as the preparation time for setting up these devices is high. Thirdly, existing procedures require repeated punctures in the patient's body for accurate positioning of the needle.

In light of the drawbacks of the existing art, there exists a need for an apparatus and a method for accurate positioning of a biopsy needle. Further, there exists a need for an apparatus and a method for accurate positioning of a needle guide such that the practitioner does not need to perform repeated insertions to reach the lesion of interest. Additionally, there is a need for an apparatus and a method that can allow biopsy insertions to be performed with minimal exposure to radiation.

BRIEF SUMMARY OF THE INVENTION

An object of the present invention is to provide a device for accurate positioning of a needle guide.

Another object of the invention is to reduce the number of punctures made on the body during biopsy procedure, thereby reducing the time of the procedure and the discomfort to the patient.

Yet another object of the invention is to provide an apparatus and a method that allows for positioning of the biopsy needle in an offline mode by using the images acquired during CT scan, without constant exposure to scanning radiations.

In accordance with the above mentioned objectives, an apparatus for accurate positioning of a needle guide is disclosed. The apparatus provides a means for taking as input the position vector of a point of insertion of the needle into the body. This point of insertion can be selected from images produced by a Computer Tomography system. Similarly, the apparatus has a means for taking as input a point of target. A controller determines the direction vector between the point of insertion and the point of target. A guide manipulator accurately positions the needle guide in line with the direction vector, such that the needle can easily be inserted through the guide to the point of target. This positioning of the guide manipulator in accordance with the direction vector is done with the help of motors.

In an embodiment of the invention, the apparatus is a multi-axis needle manipulator. The apparatus has a clamp capable of linear movement along at least one axis. Attached to the clamp is a positioning element including first and second members. The first and the second members are capable of rotating along mutually perpendicular axes. A means for determining position vectors obtains position information for the point of insertion and the point of target. A controller determines the spatial orientation of the positioning element and the clamp based on the position vectors of the point of insertion and the point of target. The needle guide is aligned to the spatial orientation through the help of a plurality of motors.

BRIEF DESCRIPTION OF THE DRAWINGS

Various embodiments of the invention will hereinafter be described in conjunction with the appended drawings provided to illustrate and not to limit the invention, wherein like designations denote like elements.

DETAILED DESCRIPTION

Accurate placement of a needle within the body can dramatically change patient management. It can help avoid invasive surgeries and minimize morbidity and mortality. Some examples of use of medical procedures that require needle insertion include: percutaneous biopsies (acquiring of tissue for pathological analysis which gives accurate diagnosis), drainage procedures (aspiration of unwanted toxic fluids from within the body), focal injection of medications (treatment of cancers and pain management), ablation of tumors (in treatment of tumors by radio frequency, cryo and laser energy), vertebral facetal injections and focused irradiation of tissues.

The invention discloses an apparatus and a method for accurate positioning of a needle guide in a patient's body. The apparatus accurately positions a needle guide with respect to a point of target within the patient's body. Such needle positioning is useful for various clinical procedures including, but not limited to, targeted medicine delivery, biopsy, bone marrow extraction, fluid biopsy, liposuction, orthopedic procedures and the like.

The apparatus, in accordance with an embodiment of the invention, provides a multi-axis manipulator, which takes scanned images of the affected portion of the body as input. The precise points of insertion and target are determined from these images. This can be done manually by an expert or can be device-assisted, through image analyzing technology. The manipulator aligns the needle guide for facilitating the easy and accurate insertion of the needle with respect to the point of target.

Figure 1:
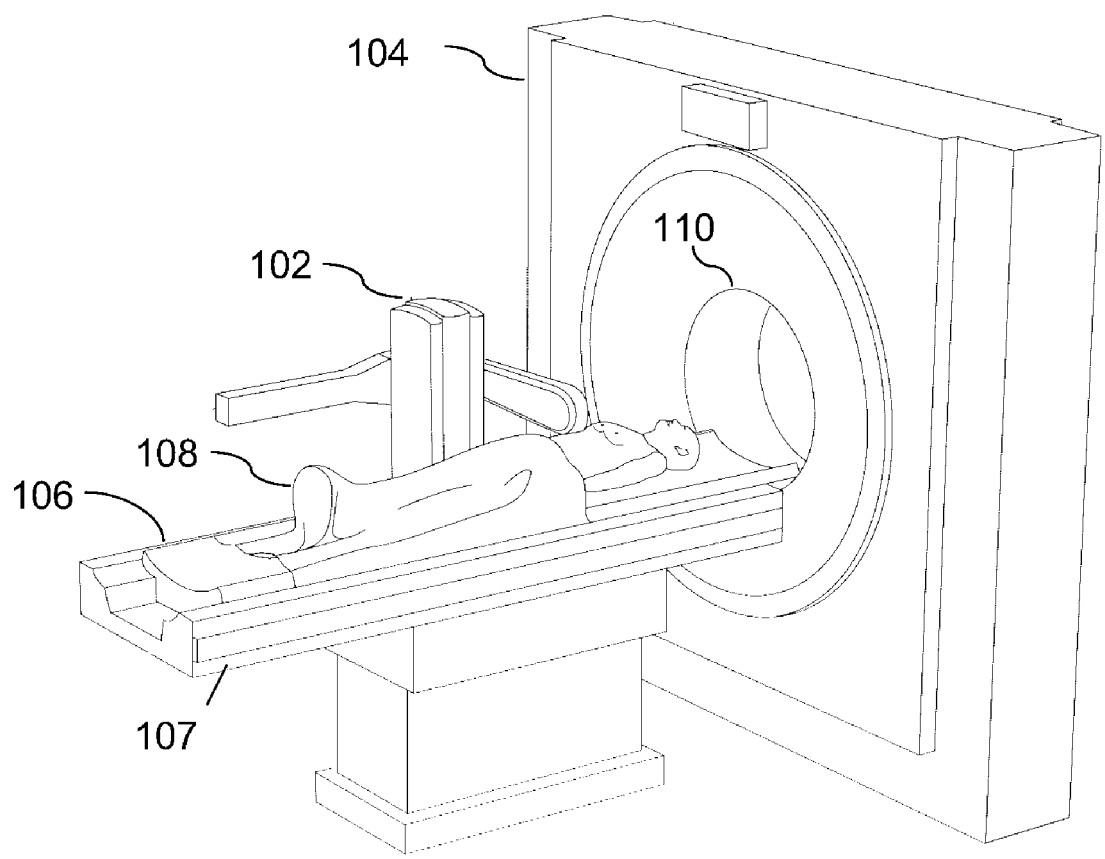
FIG. 1 shows the environment in which the apparatus of the present invention works.

FIG. 1 shows the environment in which the apparatus of the present invention works. Apparatus 102 works in conjunction with an imaging system such as a Computer Tomograph (CT) system 104. CT system 104 has a movable cradle 106 slidable over table 107. A patient's body 108 is placed on movable cradle 106 and slid into a gantry 110 for CT imaging. Inside gantry 110, images of the affected area in the patient's body 108 are taken. These images are slices of the affected area, i.e., a series of cross-section views of the affected area in the patient's body 108. For example, the images could be CT scan images of the patient's brain. CT system generates a three-dimensional image of the internals of the affected area of the patient's body 108 from a large series of two-dimensional X-ray images taken around a single axis of rotation. These series of images are also referred to as image slices. While the system of the present invention has been discussed in conjunction with a CT imaging system it will be apparent to one skilled in the art that the CT system is used for exemplary purposes only. Other systems for obtaining an image of the affected area of the patient's body 108 can also be used without deviating from the scope of the invention. For example, other imaging systems including Magnetic Resonance Imaging, Ultrasound and the like can also be used in conjunction with the present invention.

Apparatus 102 can be a standalone device that can be moved to a desired position along movable cradle 106 and locked with respect to the CT system. In an embodiment apparatus 102 can be locked with respect to the CT system using a docking system attached to a (fixed) base of movable cradle 106. Alternatively, apparatus 102 can be an integrated with the CT system. In such an embodiment, apparatus 102 leverages the motion of movable cradle 106, thereby obviating the need of linear motion of apparatus 102 with respect to movable cradle 106.

Apparatus 102 takes imaging data from the CT system in the form of DICOM images. Digital Imaging and Communications in Medicine (DICOM) is a comprehensive set of standards for handling, storing, printing, and transmitting information in medical imaging. It includes a file format definition and a network communications protocol. The communication protocol is an application protocol that uses TCP/IP to communicate between systems. DICOM files can be exchanged between two systems that are capable of receiving image and patient data in DICOM format. The DICOM images from the CT system are received by apparatus 102. Apparatus 102 facilitates the marking of the points of insertion and target on the DICOM images, and computes the coordinates for the position of the apparatus. Details of obtaining the points of insertion and target, and computing the coordinates for the position of the apparatus are discussed in conjunction with FIG. 5 and FIG. 6.

Figure 2A:
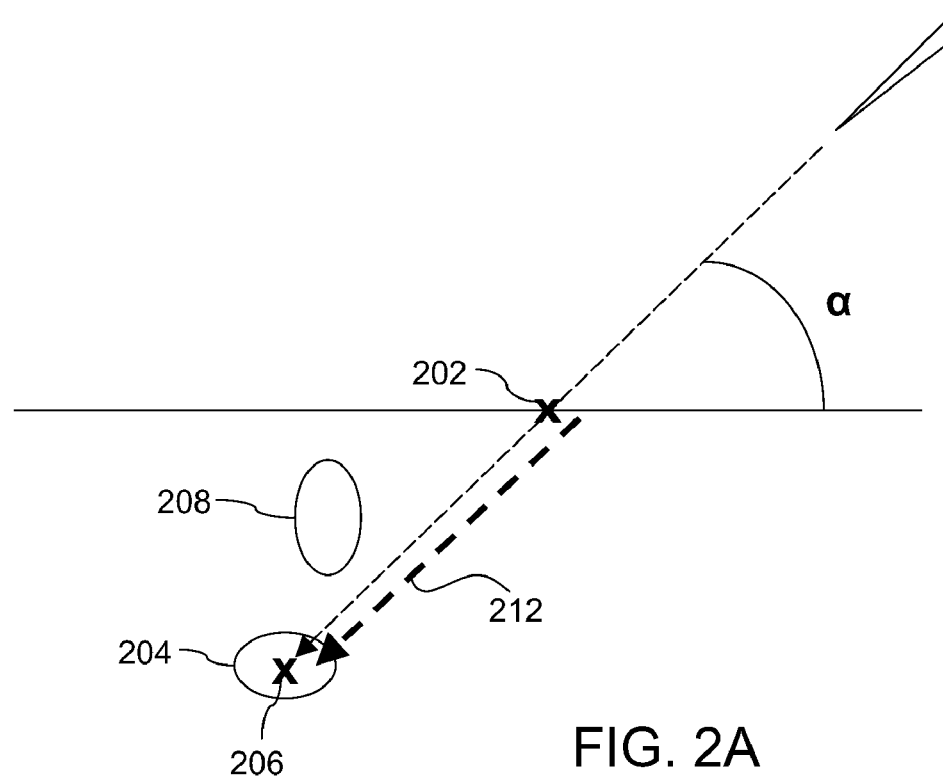
FIGS. 2A and 2B are schematics representing the insertion of a needle to a point of target in accordance with an embodiment of the invention.
Figure 2B:
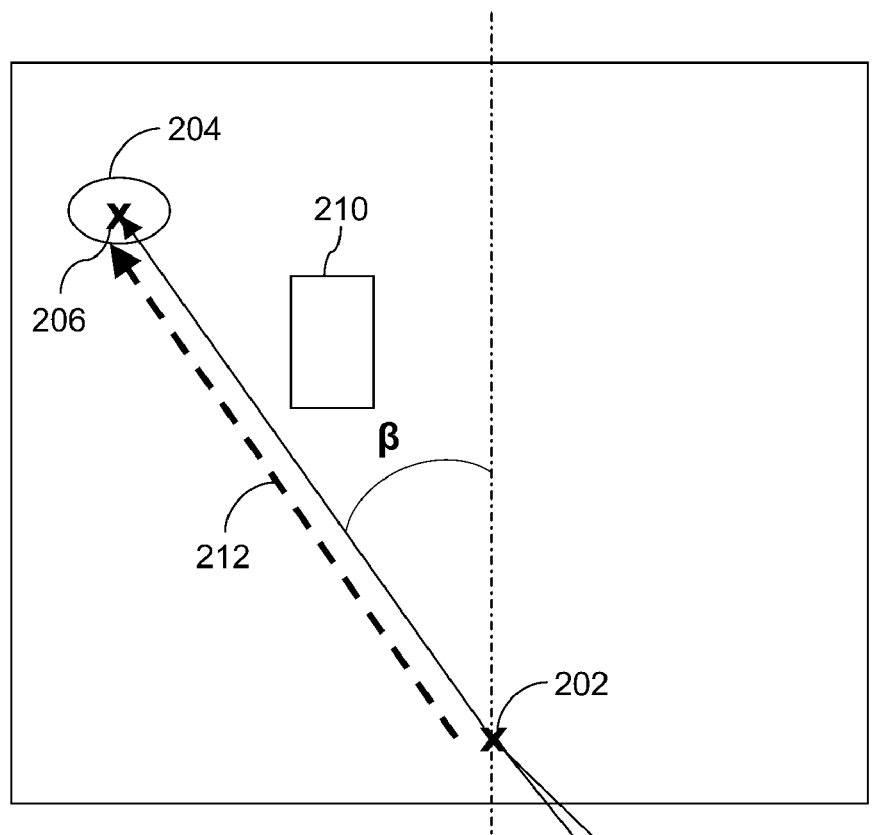

FIGS. 2A and 2B are schematics representing the procedure of needle insertion useful for clinical procedures such as biopsy in accordance with an embodiment of the present invention. FIG. 2A is a Superior Inferior (SI) plane view, while FIG. 2B is a horizontal section view of the affected portion of the patient's body 108. The needle is required to enter the patient's body 108 at point of insertion 202 and is required to touch target 204 at point of target 206. In one embodiment of the invention, target 204 is a lesion in the patient's body 108. In an alternate embodiment, target is a particular organ in the patient's body 108 for targeted delivery of medicine.

Point of insertion 202 and point of target 206 can be manually identified by a medical specialist. Point of insertion 202 and point of target 206 can also be automatically identified through image recognition techniques. Details regarding the identification of point of insertion 202 and point of target 206 are discussed in conjunction with FIG. 5. Point of insertion 202 and point of target 206 are identified such that the needle can directly reach the point of target 206 without damaging internal body parts 208 and 210 that lie in between the point of insertion 202 and point of target 206. As depicted in FIGS. 2A and 2B, the needle needs to be inserted along a direction vector 212 which is at angles $\alpha$ and $\beta$ from x and z axis respectively to ensure that it reaches point of target 206 seamlessly without affecting internal body parts 208 and 210. The direction vector 212 is difference between the position vector of point of target 206 and the position vector of point of insertion 202.

Figure 3:
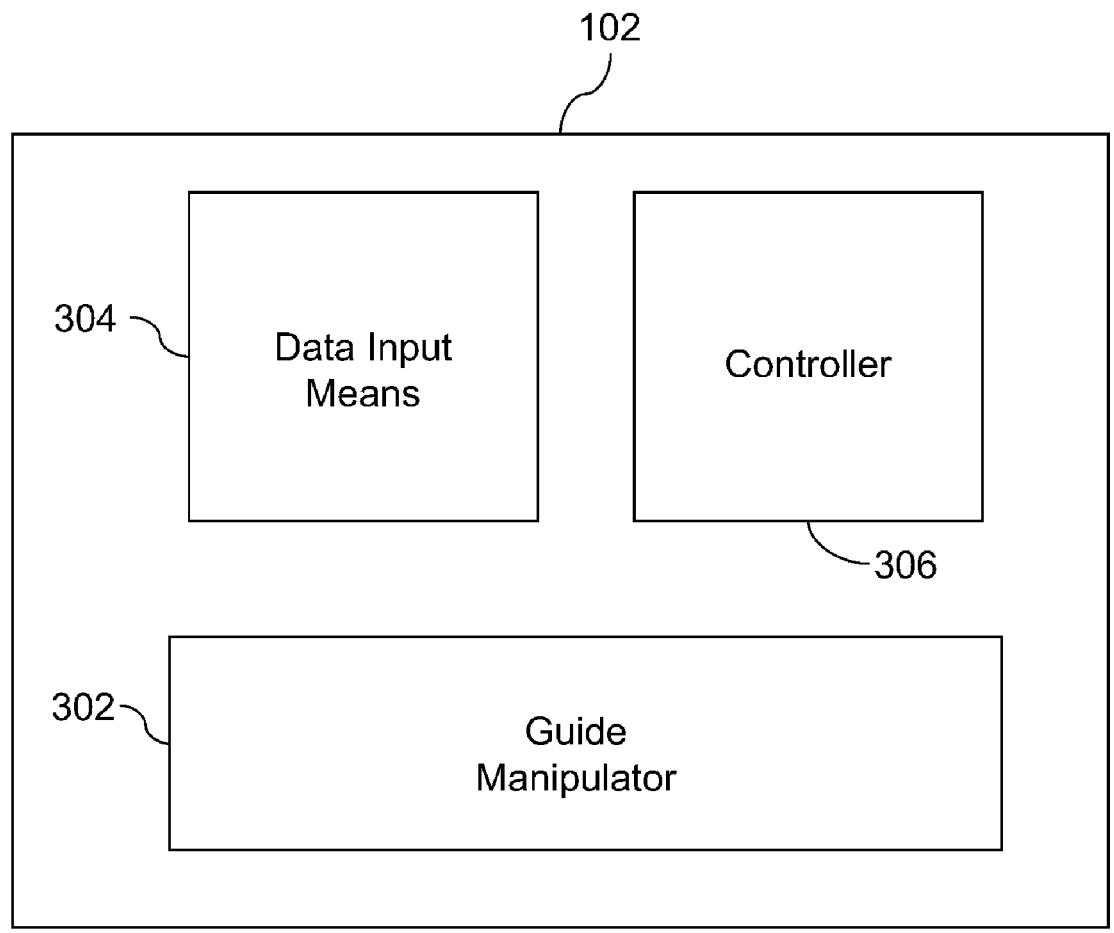
FIG. 3 illustrates an embodiment of the needle positioner in accordance with an embodiment of the present invention.

FIG. 3 illustrates the needle positioner in accordance with an embodiment of the present invention. Apparatus 102 has a guide manipulator 302, a data input means 304, and a controller 306. Data input means 304 obtains data related to the coordinates of point of insertion 202 and point of target 206. Data input means 304 has been discussed in detail in conjunction with FIG. 6. Controller 306 uses the abovementioned data related to the coordinates of point of insertion 202 and point of target 206 for determining the direction vector 212 from point of insertion 202 to point of target 206. Controller 306 further computes the spatial orientation for the needle guide to facilitate the entry of the needle into the patient's body 108 at the point of target 206. Controller 306 manipulates guide manipulator 302 to precisely align the needle guide with respect to the patient's body 108. The needle guide is positioned such that it facilitates easy insertion of the needle from point of insertion 202 to point of target 206. Guide manipulator 302 is discussed in detail in conjunction with FIG. 4. Controller 306 is discussed in detail in conjunction with FIG. 5.

Figure 4:
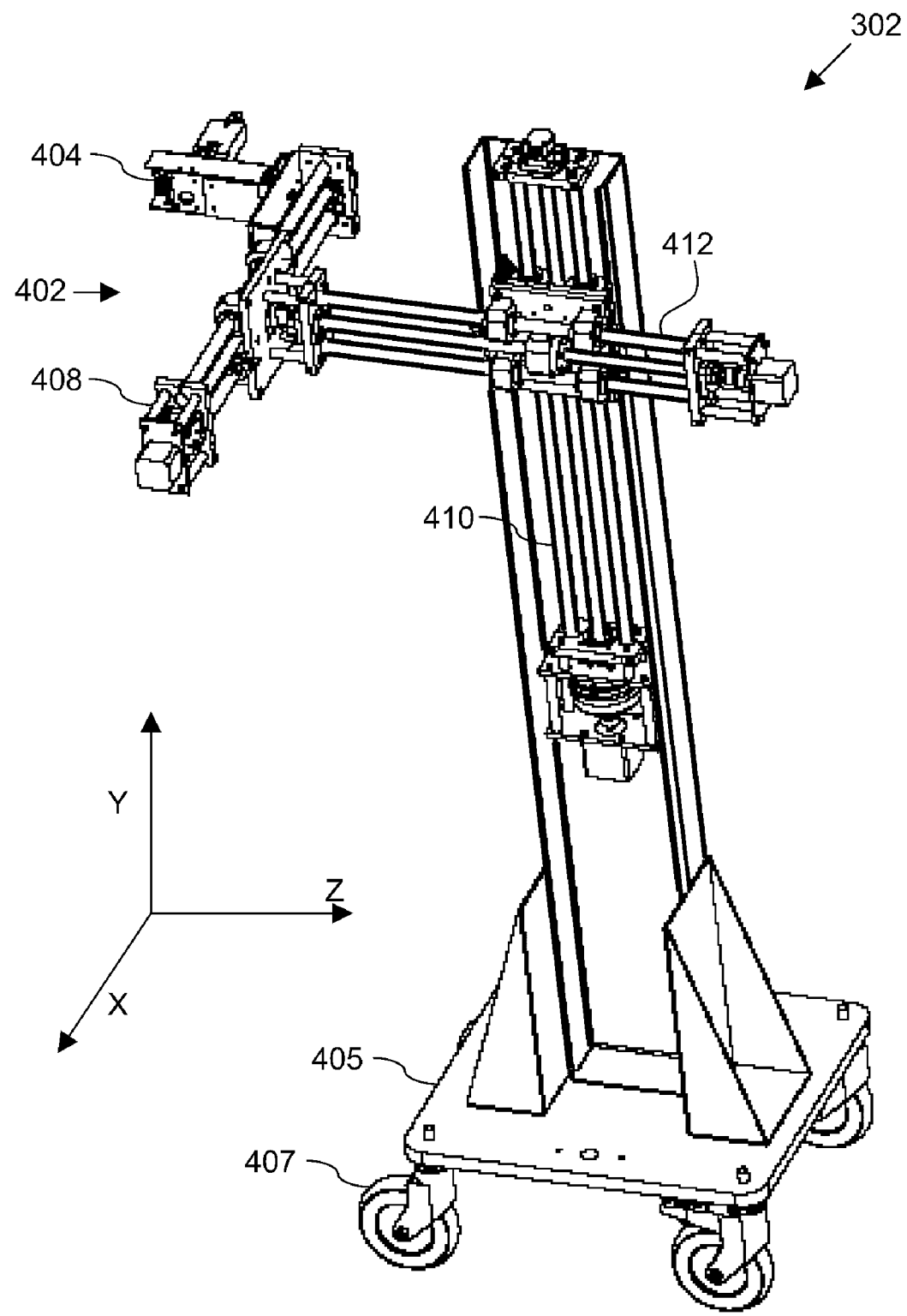
FIG. 4 is an orthogonal view of the guide manipulator in accordance with an embodiment of the invention.

FIG. 4 is an orthogonal view of guide manipulator 302 in accordance with an embodiment of the invention. Guide manipulator 302 is capable of motion in three linear directions that allows guide manipulator 302 to position the needle guide to the point of interest. Further, guide manipulator 302 can also have angular motion in two directions that facilitates the angular entry of the needle into the patient's body 108. Clamp 402 in guide manipulator 302 provides linear motion along three mutually perpendicular axes while positioning element 404 provides two angular degrees of freedom. Apparatus 102 is able to accurately position itself with respect to patient's body 108 by using the movement in these five axes.

Clamp 402 is mounted on a mobile platform 405. Mobile platform 405 is mounted on wheels 407. In one embodiment, wheels 407 are of castor type which means that the wheels are mounted with an offset steering pivot such that the wheels will automatically swivel to align themselves in the direction where they are pushed. Mobile platform 405 can be positioned near movable cradle 106 and can be locked in the desired position using a magnetic lock. Wheels 407 allow easy movement of guide manipulator 302. Mobile platform 405 can be moved manually or can be computer controlled.

In an embodiment of the invention, clamp 404 has arms 408, 410 and 412 for movement along each of the three perpendicular axes. Arm 408 provides movement along the x-axis, arm 410 provides movement along the y-axis, and arm 412 provides movement along the z-axis.

Arm 410 provides the height movement. This vertical distance is effected by ball screw-spline and stepper motors. Ball screw spline mechanism is used to provide the combination of rotation and translation on a single compact design. The ball screw mechanism can achieve three modes of motion (rotational, linear and spiral) on a single shaft by rotating and stopping the ball-screw and spline nuts through the motion coordination of two motors. The ball spline has an angular-contact structure that causes no backlash in the rotational direction, enabling precise positioning of the needle guide. Stepper motors can be interfaced to computer using few transistors and made to rotate using software. This provides further precise control over the vertical movement of the horizontal bar arms 408 and 412 by controller 306. An encoder is used to provide information on the position of the needle guide. Encoders measure the rotation of the motors to a precise degree. The encoder provides feedback to the controller 306 to precisely control the movement of the motors to an accuracy of less than 0.1 degrees.

The horizontal bar frame has two bar frame arms 408 and 412. The bar frame arms are attached in an L-shape such that they can slide perpendicular to the each other. The horizontal bar system provides motion in x and z direction. A positioning element 404 is attached to the horizontal bar frame. Positioning element has been illustrated in detail in FIG. 5.

In an embodiment of the invention, a distance measurement sensor is provided to measure distance of the cradle from the point of insertion in order to position the guide manipulator accurately.

A docking system is provided to dock guide manipulator 302 accurately with respect to gantry 110. The docking system also ensures parallel alignment of the guide manipulator with respect to table 107. Apparatus 102 is connected to a controller 306 that controls the motion of guide manipulator 302 and clamp 402. Details of controller 306 are discussed in conjunction with FIG. 5.

Figure 5A:
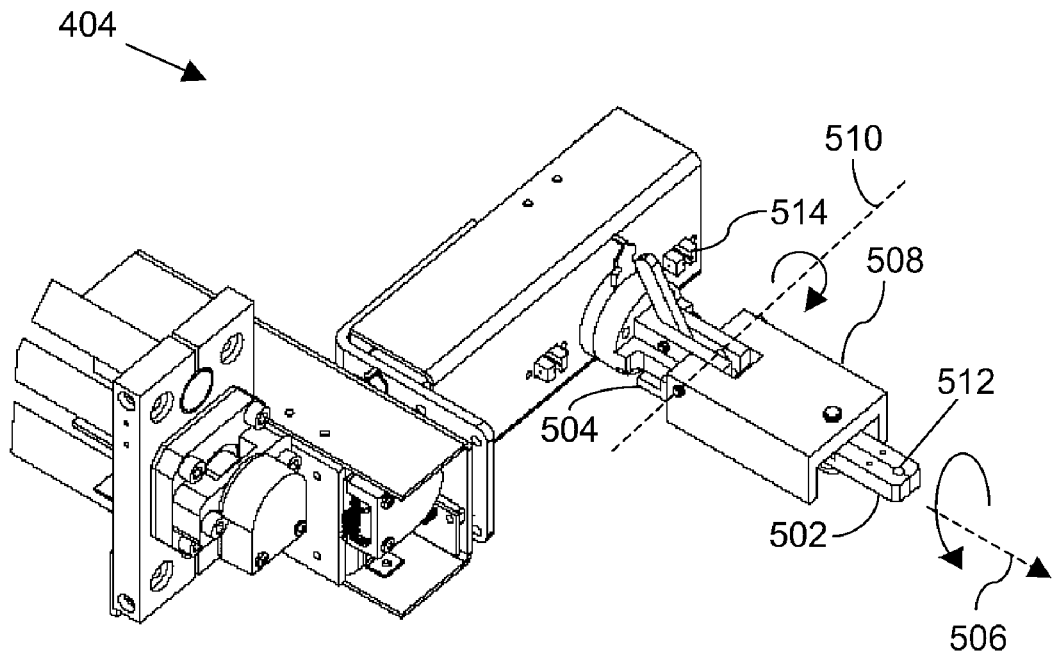
FIG. 5 depicts an orthogonal view of the positioning element in accordance with an embodiment of the invention.
Figure 5B:
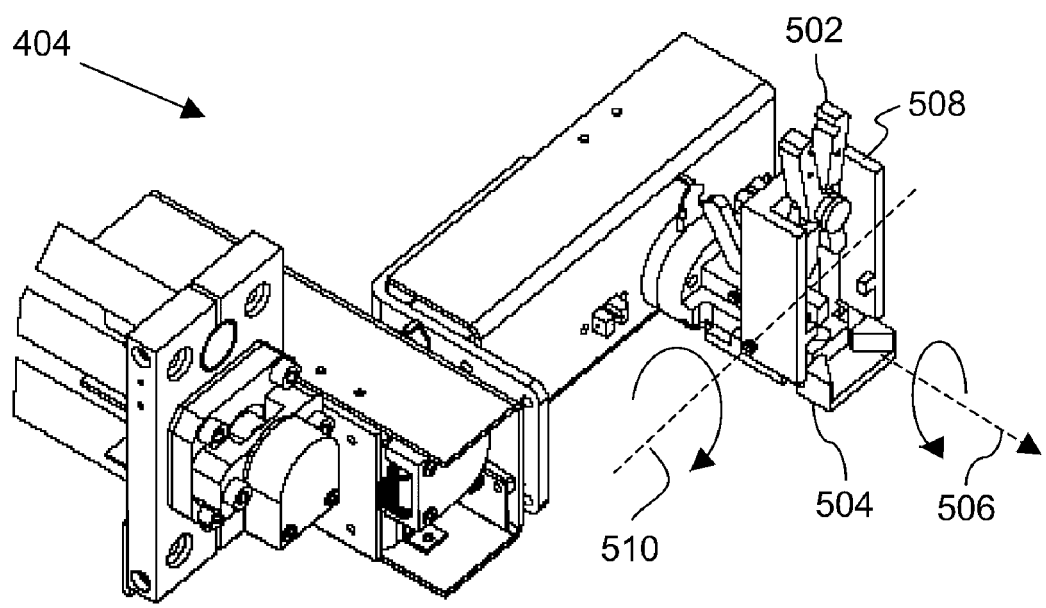

FIGS. 5A and 5B depict two orthogonal views of the positioning element. Positioning element 404 provides angular movement of a needle guide 502. Positioning element 404 comprises two components—a first member 504, capable of rotating about a first axis 506, and a second member 508 capable of rotating about a second axis 510. Axes 506 and 510 are mutually perpendicular. FIGS. 5A and 5B show two different orientations of member 508. In FIGS. 5A and 5B needle guide 502 is shown in closed (gripped) and release positions respectively.

Needle guide 502 is attached to second member 508. Needle guide 502 holds the needle firmly in slot 512. Needle guide 502 also has a needle release knob 514. After the needle has been inserted into the patient's body 108, needle release knob 514 is actuated to release the needle. This can be done either manually or automatically. As the needle release knob 514 is actuated, it releases the needle from the guide manipulator 302.

The rotational motion about axes 508 and 510 helps in orienting needle guide 502 along the computed direction vector 212. This enables a surgeon to precisely insert the needle through second member 508 along the computed position vector to reach the point of target. This obviates the need for repeated incision in the patient's body 108 to reach the target.

Figure 6:
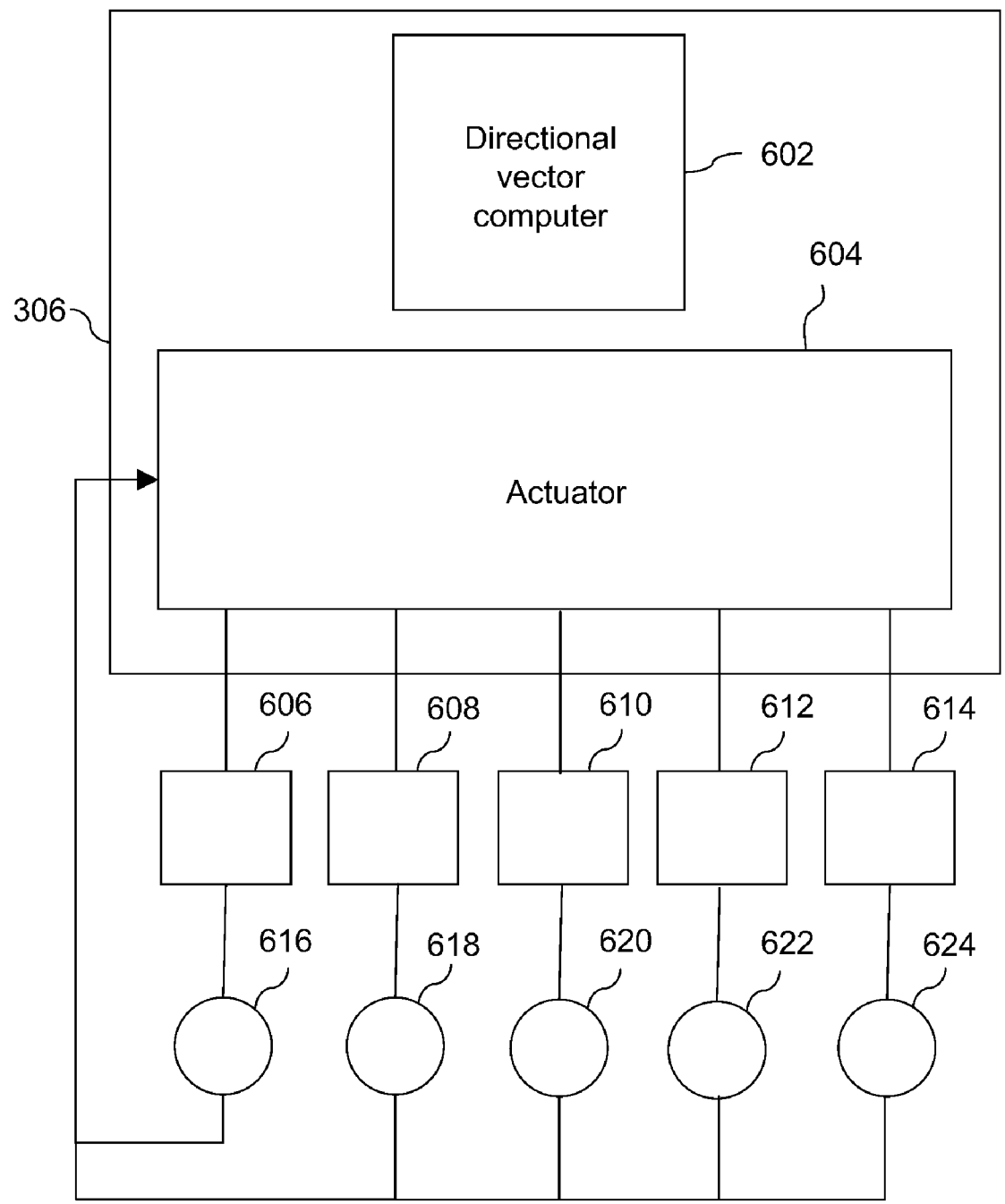
FIG. 6 is a schematic of the controller in accordance with an embodiment of the invention.

FIG. 6 is a schematic of controller 306 in accordance with an embodiment of the invention. Controller 306 has a directional vector computer 602 and an actuator 604. Directional vector computer 602 determines the linear position of clamp 402, and the angular position of positioning element 404. Directional vector computer 602 computes the spatial orientation of needle guide 502 using point of target 206 and point of insertion 202. In particular, directional vector computer 602 determines the linear position (x, y, z) and the angular position ($\alpha$, $\beta$) for apparatus 102. Details of the algorithm used in directional vector computer 602 are discussed in conjunction with FIG. 7. Actuator 604 is used for controlling motors 606-614. Motors 606-614 move the arms of guide manipulator 302 to align them in accordance with computed spatial orientation of guide manipulator 302 with the help of encoders 616-624. Encoders 616-624 provide feedback to controller 306 on the precise degree of movement of clamp 402 and positioning element 404. In particular, motors 606-614 provide the linear movement of clamp 402 in the x, y and z axis, and the angular movement of positioning element 404 along the two rotational axes. It will be apparent to one skilled in the art that although five motors have been shown in the embodiment of FIG. 6, there could be fewer than or more than five motors in the apparatus without deviating from the scope of the invention.

Figure 7:
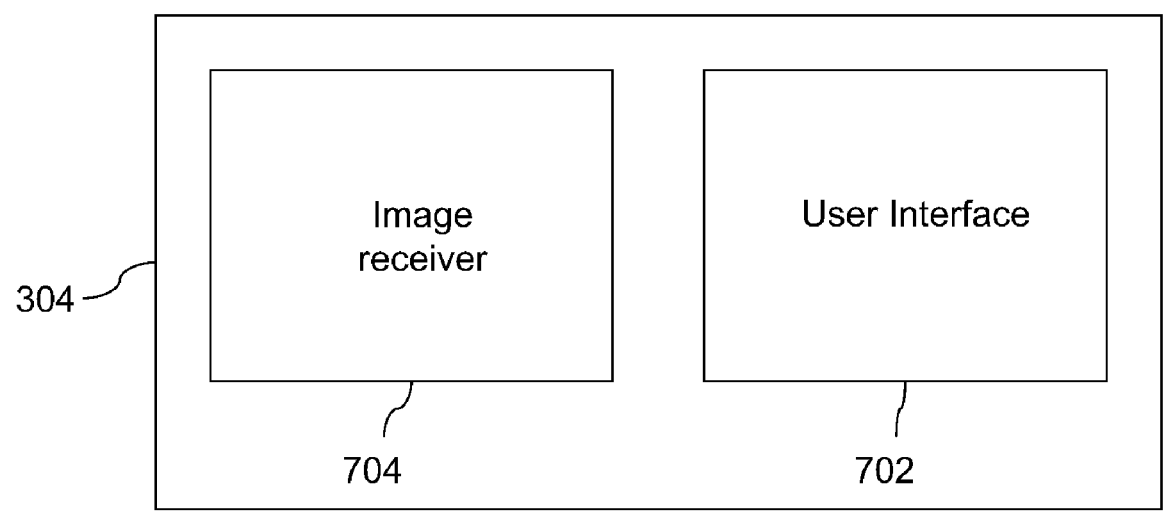
FIG. 7 is a schematic of the data input means in accordance with an embodiment of the invention.

FIG. 7 is a schematic of Data input means 304 in accordance with an embodiment of the invention. Data input means 304 has a User Interface 702, and an image receiver 704. User Interface (UI) 702 provides for input of various movement coordinates for apparatus 102. UI 702 also displays the current position of each axis after positioning using feedback mechanism. Image receiver 704 acquires DICOM images from CT system 104. UI 702 displays the received DICOM images. UI 702 also allows for input of point of target 206 and point of insertion 202 on the DICOM images. Such input can be provided by a radiologist, or other medical practitioners. Alternatively, point of target 206 and point of insertion 202 can be determined automatically through the use of advanced image recognition technology. It will be apparent to a person skilled in the art that the point of target 206 and point of insertion 202 may be determined using any other approach without deviating from the scope of the invention.

Figure 8A:
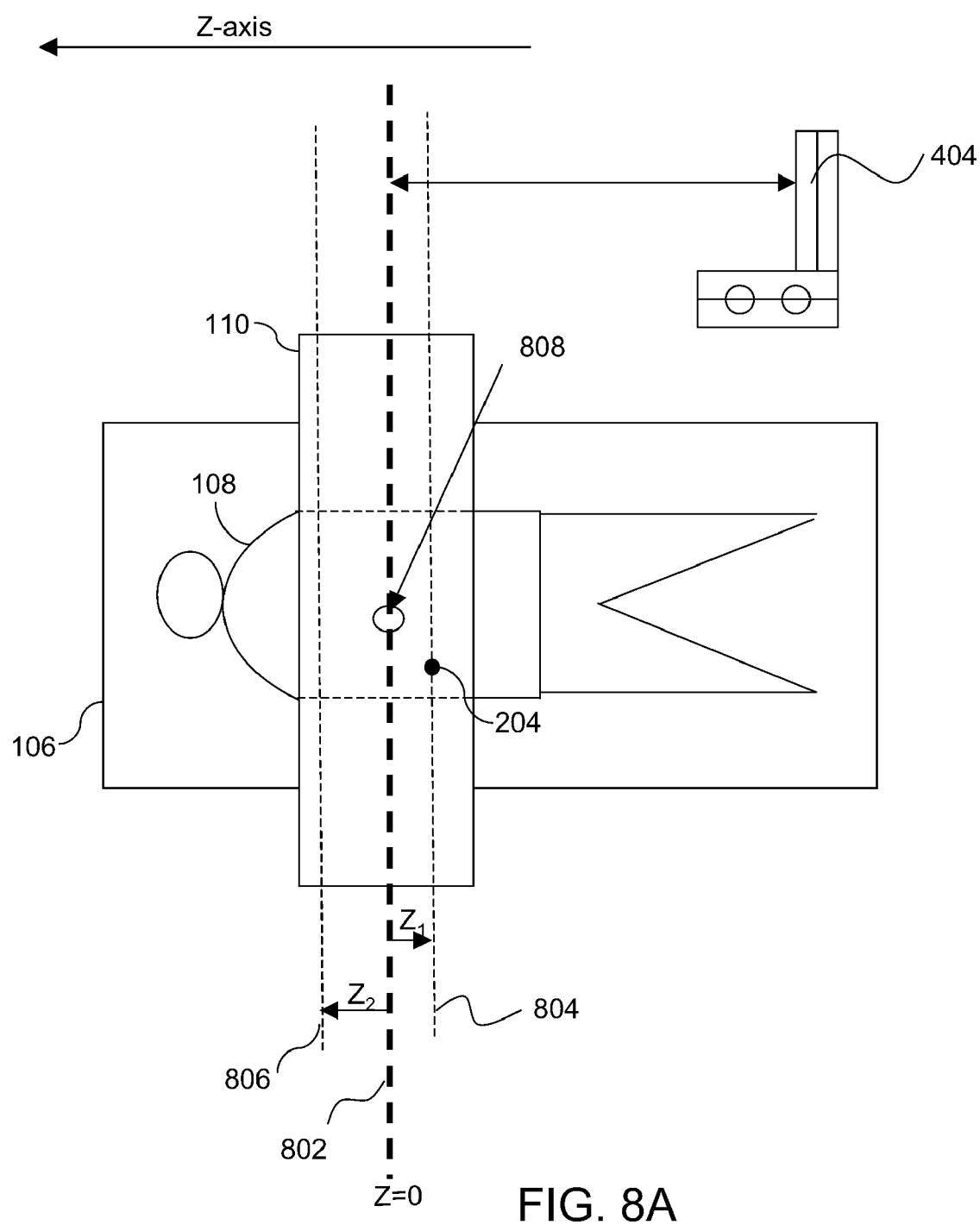
FIGS. 8A, 8B, 8C, and 8D illustrate the computation of the direction vector for aligning the needle guide.

FIGS. 8A, 8B, 8C and 8D are a series of illustrations depicting the computation of direction vector 212 for aligning needle guide 502. In accordance with an embodiment of the invention, the coordinate system used is the Cartesian system. The center of CT gantry 110 is chosen as the gantry zero 808 (origin: x=0, y=0, z=0) of the coordinate system. The coordinates of point of insertion 202 are (x2, y2, z2) and point of target 206 are (x1, y1, z1). FIG. 8A depicts the initial position of the system. The horizontal direction of movement of movable cradle 106 in and out of gantry 110 is designated as the z-axis. Gantry zero 808 is essentially the z=0 level 802. The CT scan provides image slices of the body at different vertical sections. From the series of image slices, the image slice for point of target 804 (z=z1) and the image slice for point of insertion 806 (z=z2) are identified. Axis 804 is a vertical section of the body at point of target 202 denoted as (x2, y2, z2). Axis 806 is a vertical section of the body at point of insertion 206 denoted as (x1, y1, z1).

Figure 8B:
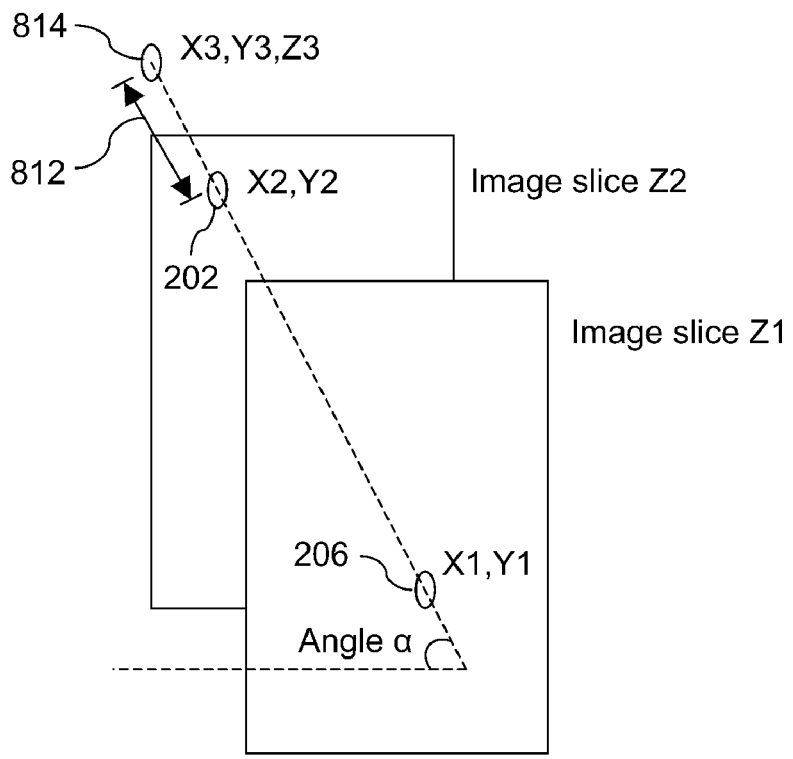

FIG. 8B shows the image slices of different sections of the body. A lateral scout view, with the planes of each CT slice indicated, is included in the scanned image. It indicates the z-distance (z-coordinates) for the frames. It shows the front view of the slices at 804 (z=z1) and 806 (z=z2). Coordinates (x1, y1, z1) and (x2, y2, z2) are coordinates seen on the image slices. The spatial coordinates of needle guide 502 is 814 (x3, y3, and z3). This position is offset from the surface of the body of the patient by a dead space 812. A corresponding spatial orientation in the actual patient's body 108 is determined by the following formula:

$X$ value in mm=((Graphical $X$–$X$Offset)/ZoomValue) *pixel-spacing;

$Y$ value in mm=((Graphical $Y$–$Y$Offset)/ZoomValue) *pixel-spacing;

$Z$ value in mm=slice-location from DICOM header;

Where,
Graphical X=x1, or x2, or x3;
Graphical Y=y1, or y2, or y3; and,
Graphical Z=z1, or z2, or z3.

In the above formula, XOffset and YOffset are the offsets introduced in x and y values due the dead space between the patient's body and needle guide created due to the construction of the device. Zoom value indicates the magnification value. It is the ratio of the size of the image displayed on the screen to the actual size of the image.

Pixel spacing is the spacing between the pixels on the UI. The pixel spacing depends upon the size of the screen and the number of pixels that are present on the screen area.

Figure 8C:
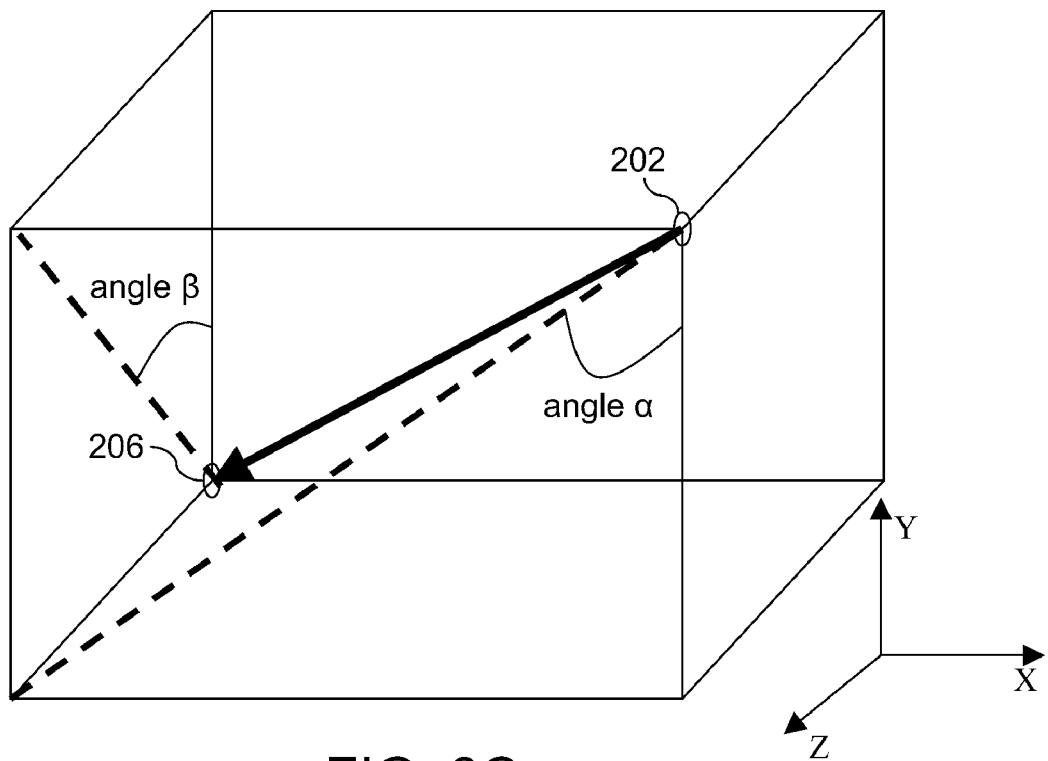
Figure 8D:
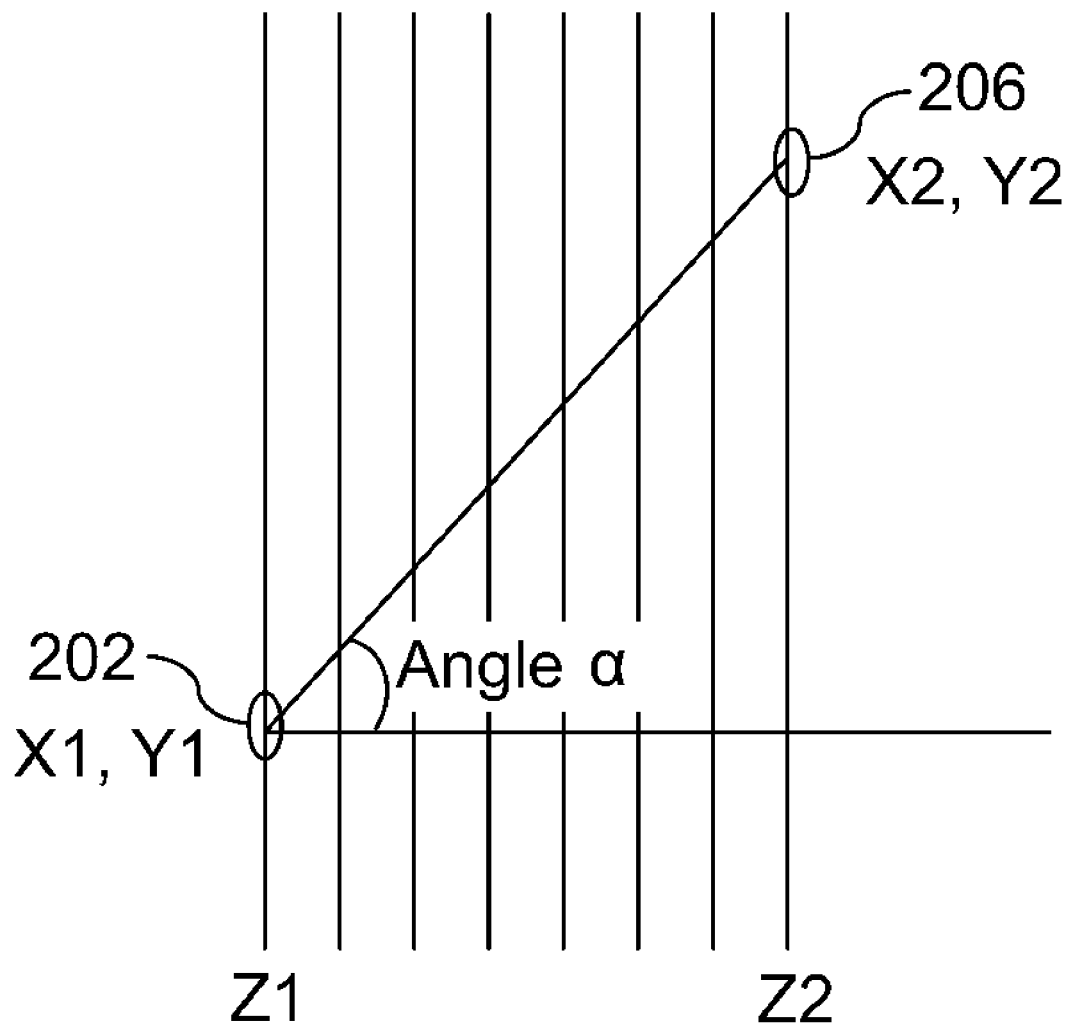

After computing the coordinates for point of insertion 202 and point of target 206 in real environment, the distance between the two points is determined using the distance formula $d=(\Delta X^2+\Delta Y^2+\Delta Z^2)^{1/2}$ where $\Delta X$, $\Delta Y$ and $\Delta Z$ are the differences in X, Y and Z coordinates of point of target 206 and point of insertion 202, i.e.,
$\Delta X=x1-x2$
$\Delta Y=y1-y2$
$\Delta Z=z1-z2$ Further the orbital angles alpha and beta are determined by
alpha=a tan (ydiff/xdiff)
beta=a tan (zdiff/ydiff)
where the angles alpha and beta are as shown in FIG. 8C.

These angles determine the rotational values by which member 504 and member 508 must be rotated so as to align needle guide 502 along direction vector 212.

Needle slot 512 is positioned at 814 with coordinates (x3, y3, z3). Guide manipulator 302 which is docked to the docking system is thus at a known distance from gantry zero 808. The needle pointer is placed at a distance equal to dead space 812 from point of insertion 202 determined. Hence the coordinates are adjusted for dead space 812 using $x3,y3,z3=x2,y2,z2$+Dead space 812

In an embodiment of the invention, guide manipulator 302 positions itself in such a way that only a pre-determined portion of the needle is inserted into the body. This is done by determining the length of the needle to be used and the distance between point of target 206 and point of insertion 202. The doctor then chooses the dead space 812, which is communicated, to controller 306. Controller 306 computes coordinates 814 (x3, y3, z3) and thus the three coordinates, viz. point of insertion 202, point of target 206 and the location of the needle guide 502, are determined.

Although the above description of the computation of the direction vector 212 is shown in Cartesian coordinates system, it must be apparent to a person skilled in the art that any other coordinate system can be used without deviating from the scope of the invention. For example, point of insertion 202 and point of target 206 can be determined and expressed in coordinate systems like Cartesian, Polar, Spherical, curvilinear and the like or in a combination of one or more of these coordinate systems.

Figure 9A:
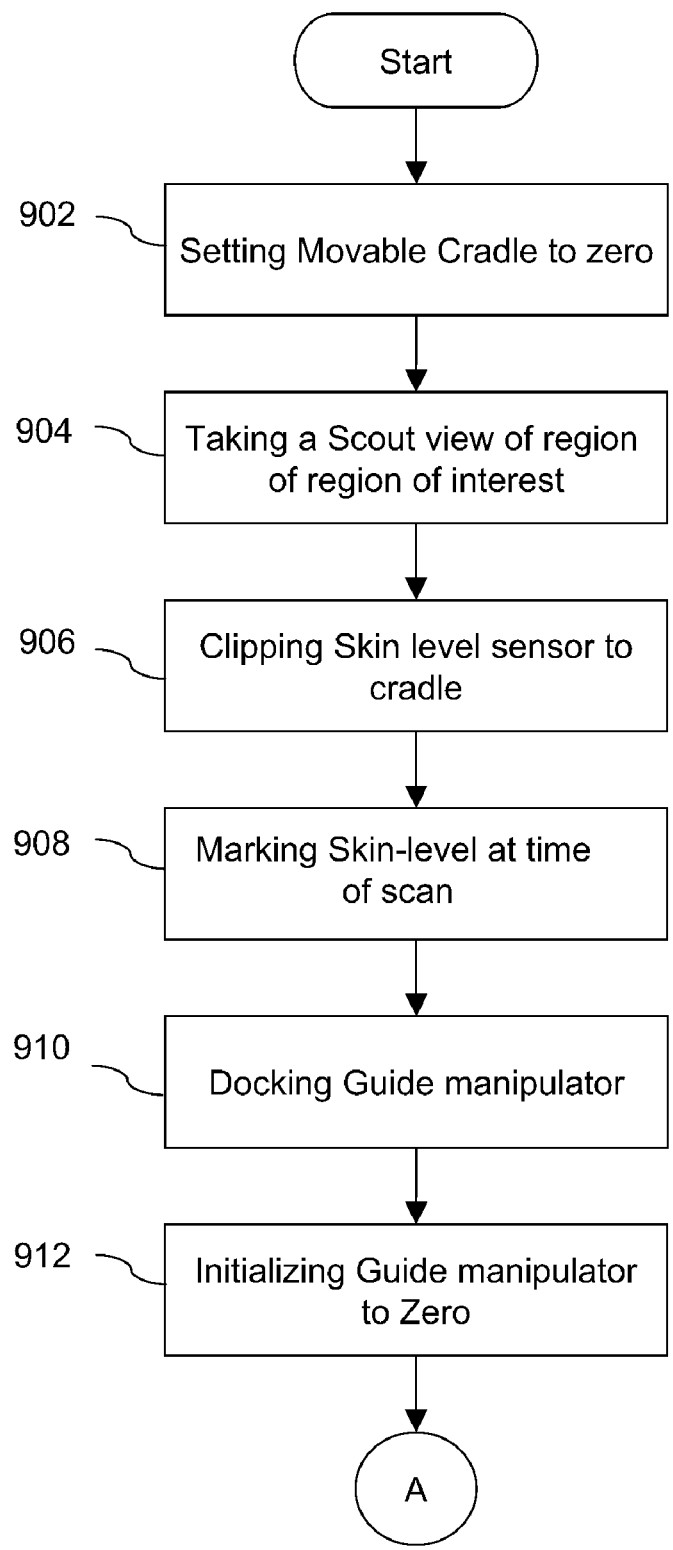
FIG. 9 is a flow chart illustrating the method to position a needle guide in accordance with an embodiment of the invention.
Figure 9B:
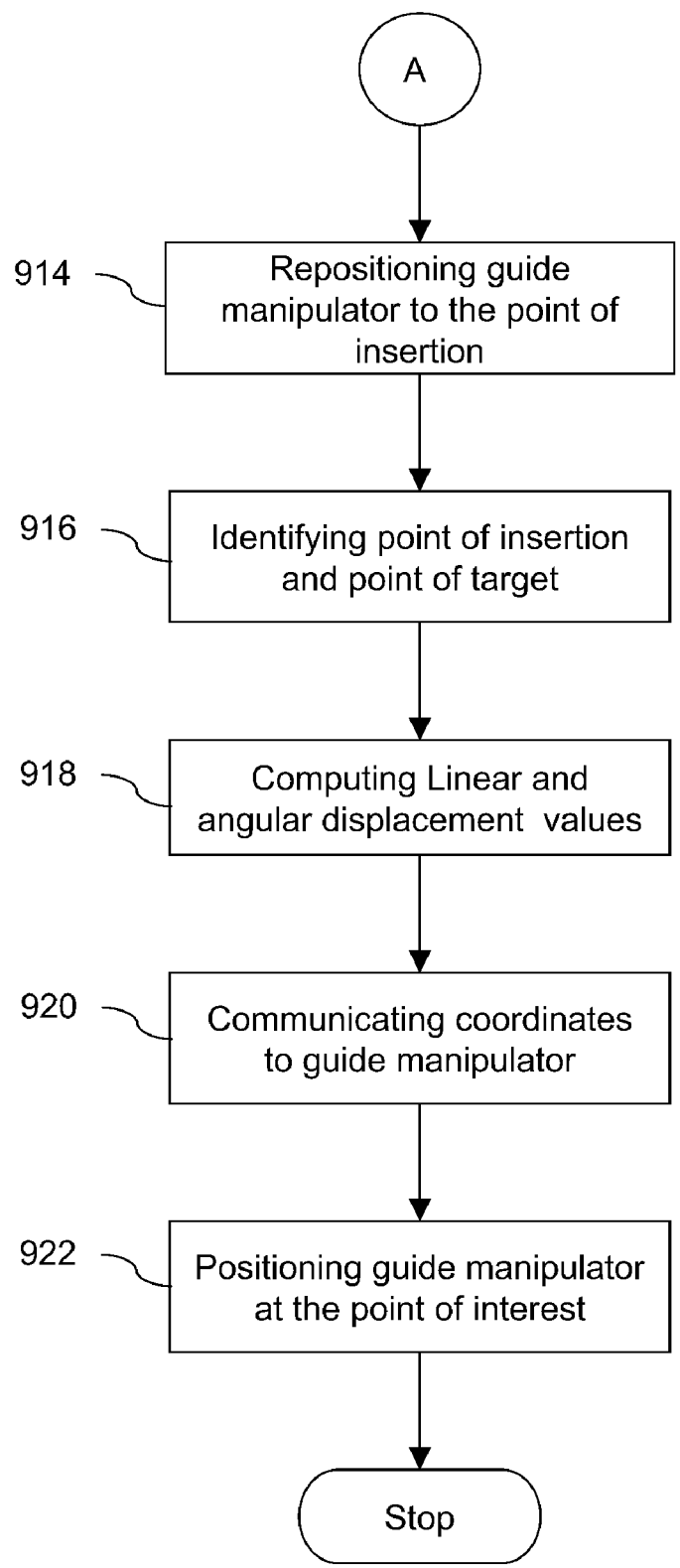

FIG. 9 is a flowchart illustrating the method of positioning a needle guide 502 in accordance with an embodiment of the invention. At step 902, movable cradle 106 is set to zero. This is done by moving the region of interest of the patient into gantry 110. The region of interest is the area around which the lesion is expected to be present. At step 904 a scout view of the region of interest is taken. At step 906 a slain level sensor is clipped onto movable cradle 106 at the identified region away from the scan range. Details of the skin level sensor are discussed in conjunction with FIG. 10. The position of skin surface at the time of the scan is marked through the use of the skin level sensor at step 908. This is done by asking the patient to hold breath during the time of the scan. At step 910, guide manipulator 302 is docked to a docking rail. Thereafter at step 912, guide manipulator 302 is initialized to zero position along all axes. Movable cradle 106 is moved to a point where biopsy procedure could be carried out conveniently on the patient's body 108.

At step 914, the guide manipulator 302 repositions itself to point of insertion 202. This is achieved by moving the guide manipulator 302 by a distance equal to the distance of the position of insertion 202 from the gantry zero 808.

Thereafter at step 916, the point of insertion 202 and the point of target 206 are identified. This is done by acquiring the CT image slices into the system using a DICOM interface. In an embodiment of the invention, the points of insertion and the point of target are identified manually through a User Interface (UI) console by a medical practitioner, such as a doctor, radiologist and the like. Alternatively, the point of insertion and the point of target can be determined automatically through the use of image recognition technology. It will be apparent to a person skilled in the art that any other method can be used to determine the point of insertion and the point of target, without deviating from the scope of the invention.

At step 918, the linear and angular displacement values for the guide manipulator 302 are computed. In an embodiment of the invention, guide manipulator 302 can be positioned along five axis, three axes of linear motion (x, y, z) and two axes of angular motion ($\alpha$, $\beta$). The coordinates x, y and z, and the angles $\alpha$ and $\beta$ are computed by controller 306. At step 920, the coordinates are communicated to the guide manipulator 302. In an embodiment of the invention, this communication is achieved through an RS 232 or any other data communication interface. At step 922, guide manipulator 302 is positioned in accordance with the computed linear and angular displacement values.

Once needle guide 502 has been positioned, it can be used for conducting a biopsy procedure. A first set of co-ordinates are communicated to position the guide manipulator 302 at a predefined height and to point a laser light to make an incision on the patient's body 108 at the needle entry point. The surgeon makes an incision at the point of laser light. After this, a 'position for Biopsy' button is pressed in guide manipulator 302. Thereafter, the next set of coordinates is communicated to position needle guide 502 close to patient's body 108. Skin surface position of the patient's body is monitored in the breath sensor console and the patient is asked to hold breath at that position. The surgeon inserts the needle to the depth indicated in the UI console or to the full length based on the option selected when analyzing the image slice for marking the points of insertion 202 and the point of target 206. The needle release knob is actuated and the needle is made free from the guide manipulator 302. A check scan is performed to confirm the position of the needle. In an embodiment of the invention controller 306 allows the practitioner to visualize the needle trajectory in the images. The Check scan data from the CT system is acquired and the simulated versus actual position of needle and the line of the needle is shown. Thereafter the surgeon checks to confirm the position of the needle tip. When the position is found to be correct, then the biopsy procedure is performed.

Figure 10:
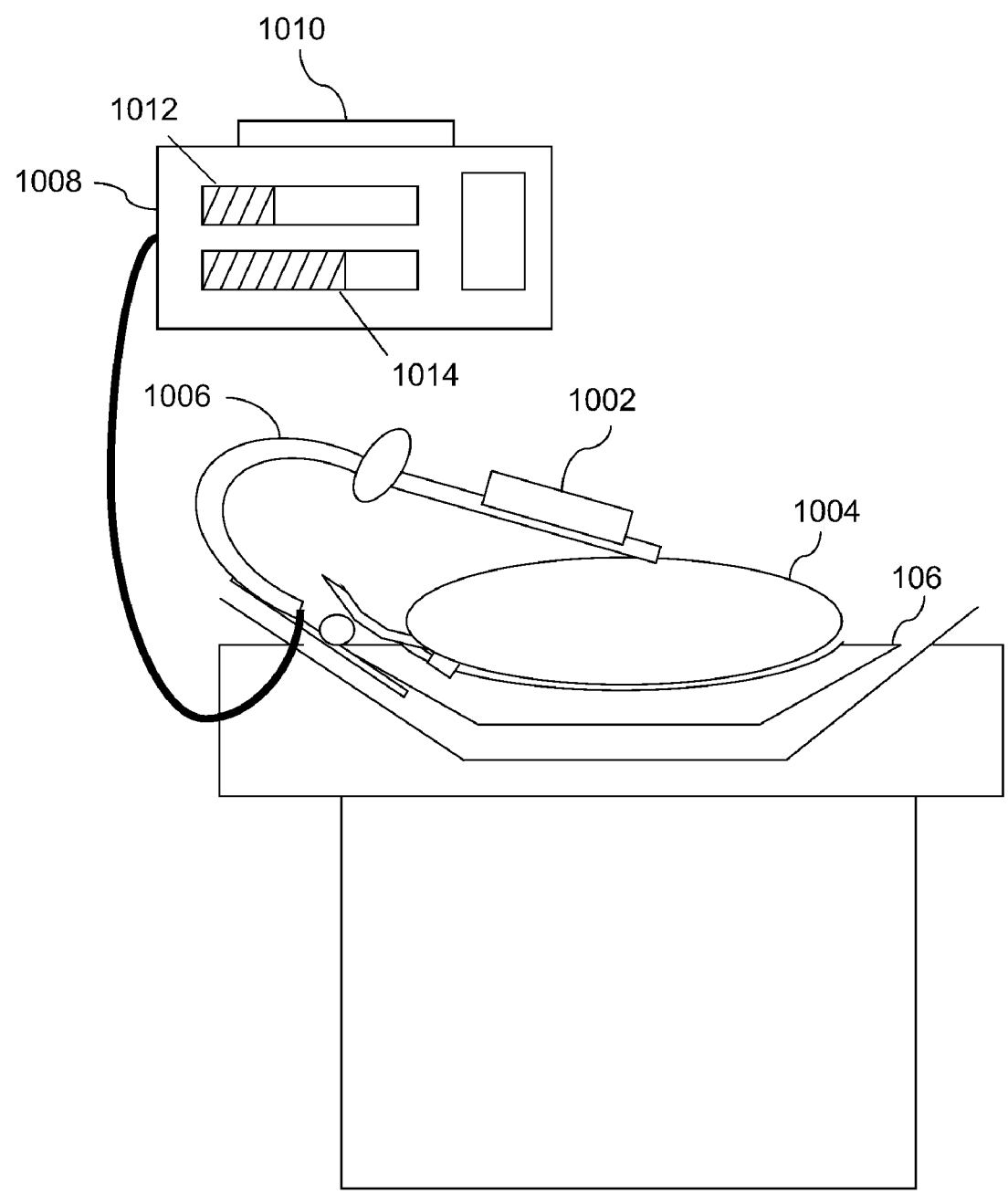
FIG. 10 illustrates a skin level sensor for providing correction to the spatial orientation of the needle guide, in accordance with an alternative embodiment of the invention.

FIG. 10 illustrates a skin level sensor for providing correction to the spatial orientation of needle guide 502, in accordance with another embodiment of the invention. The skin level sensor can be a breath sensor. A breath sensor 1002 is placed on abdomen 1004 of the patient. Breath sensor 1002 is attached to movable cradle 106 through cradle clip 1006. A breath level indicator 1008 is attached to breath sensor 1002. Breath level indicator 1008 has a freeze key 1010 for capturing the position of abdomen 1004 at the point of the CT imaging.

The patient is asked to hold breath just before the initial target identification scan. Breath level indicator 1008 shows a bar graph and the surgeon freezes the position of the skin level at the time of taking the scan. This freeze point is indicated as graph 1012. The patient scan is taken and then the patient is allowed to breathe normally. After positioning the needle guide, and just before the needle is inserted into the patient, the patient is asked to hold the breath again. Breath level indicator 1008 indicates the level of the skin in graph 1014. The needle insertion procedure is conducted as long as graph 1014 remains within a predefined tolerance zone of graph 1012. If before needle insertion, the patient releases the breath such that graph 1014 moves outside of the predefined tolerance zone, an audio alert is sounded and the patient is asked to hold the breath again.

In an embodiment of the present invention, a plane level indicator is provided at the base of guide manipulator 302 to account for any non-planar nature of the surface of mounting of guide manipulator 302.

Controller 306 and data input means 304, as described in the current invention or any of its components, may be embodied in the form of a processing machine. Typical examples of a processing machine include a computer, a programmed microprocessor, an integrated circuit, and other devices or arrangements of devices that are capable of implementing the steps of the method of the current invention.

The processing machine executes a set of instructions that are stored in one or more storage elements, in order to process input data. The storage elements may also hold data or other information as desired. The storage element may be in the form of an information destination or a physical memory element present in the processing machine.

The set of instructions may include various commands that instruct the processing machine to perform specific tasks such as the steps that constitute the method of the present invention. The set of instructions may be in the form of a software program. The software may be in various forms such as system software or application software. Further, the software might be in the form of a collection of separate programs, a program module with a larger program or a portion of a program module. The software might also include modular programming in the form of object-oriented programming. The processing of input data by the processing machine may be in response to user commands, or in response to results of previous processing or in response to a request made by another processing machine.

A person skilled in the art can appreciate that the various processing machines and/or storage elements may not be physically located in the same geographical location. The processing machines and/or storage elements may be located in geographically distinct locations and connected to each other to enable communication. Various communication technologies may be used to enable communication between the processing machines and/or storage elements. Such technologies include session of the processing machines and/or storage elements, in the form of a network. The network can be an intranet, an extranet, the Internet or any client server models that enable communication. Such communication technologies may use various protocols such as TCP/IP, UDP, ATM or OSI.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

What is claimed is:

1. An apparatus, comprising:
a support base configured to be movable to a desired position on a floor adjacent a movable cradle of an imaging system and lockable at the desired position relative to the imaging system;
a guide manipulator supported on the support base, the guide manipulator configured to position a needle guide at a target location with respect to a patient disposed on the movable cradle, the target location being outside an imaging space of the imaging system such that a needle can be inserted through the needle guide at the target location, through an insertion point on the patient, and into a target point within the patient; and
processing circuitry configured to:
receive images of the patient from the imaging system;
determine, based at least in part on the received images, a location of the insertion point relative to a gantry of the imaging system when the patient is disposed on the movable cradle and the movable cradle is disposed outside of the imaging space of the imaging system such that the insertion point is outside of the imaging space;
determine a directional vector between the insertion point and the target point;

determine the target location of the needle guide to be in line with the directional vector based at least in part on the determined location of the insertion point and the directional vector; and cause the guide manipulator to be moved to position the needle guide at the target location.

2. The apparatus of claim 1, wherein the support base is selectively lockable to a docking system.

3. The apparatus of claim 1, wherein the target location of the needle guide is determined at least in part based upon a position of the support base with respect to the imaging system.

4. The apparatus of claim 1, wherein the processing circuitry is configured to determine the target point within the patient based at least in part on the images received from the imaging system, and the target location of the needle guide is determined at least in part based on the insertion point and the target point and coordinates derived from the desired position of the support base with respect to the imaging system.

5. The apparatus of claim 1, wherein the guide manipulator includes a positioning element, the positioning element including first and second members, the first and second members configured to rotate about mutually perpendicular axes.

6. The apparatus of claim 1, further comprising a skin level sensor adapted to be disposed on a skin surface of the patient and to provide signals to the processing circuitry indicating whether a correction of a spatial orientation of the needle guide is needed.

7. The apparatus of claim 1, wherein the guide manipulator has five axes of movement.

8. The apparatus of claim 1, further comprising a display portion coupled to the processing circuitry and configured to display image data received from the imaging system.

9. The apparatus of claim 1, wherein the imaging system is a computed tomography system.

10. The apparatus of claim 1, wherein the processing circuitry is configured to determine the target location of the needle guide based at least in part upon a length of a needle to be inserted through the needle guide such that a predetermined portion of the length of the needle can be inserted relative to the needle guide, through the insertion point, and into the target point.

11. The apparatus of claim 1, wherein the processing circuitry is configured to determine the insertion point and the target point based at least in part on the images received from the imaging system, and the target location of the needle guide is determined at least in part based on the insertion point and the target point and a length of a needle to be inserted through the needle guide such that a predetermined portion of the length of the needle can be inserted relative to the needle guide, through the insertion point, and into the target point.

12. The apparatus of claim 1, wherein the processing circuitry is configured to position the needle guide at the target location such that the needle guide is in a fixed position relative to the patient and such that a needle can be inserted through the needle guide and moved relative to the needle guide.

13. An apparatus, comprising:
a mobile support base configured to be positionable at a location relative to an imaging system;
a guide manipulator supported on the support base and configured to position a needle guide at a target location with respect to a patient disposed on the movable patient cradle when the support base is at the location relative to the imaging system, the target location being outside an imaging space of the imaging system such that a needle can be inserted through the needle guide at the target location, through an insertion point on the patient, and into a target point within the patient; and processing circuitry configured to:
determine the location relative to the imaging system in which the support base is to be positioned;
receive images of the patient from the imaging system;
determine, based at least in part on the received images, a location of the insertion point relative to a gantry of the imaging system when the patient is disposed on the movable cradle and the movable cradle is disposed outside of the imaging space of the imaging system such that the insertion point is outside of the imaging space;
determine a directional vector between the insertion point and the target point;
determine the target location of the needle guide to be in line with the directional vector based at least in part on the determined location of the insertion point and the directional vector; and
cause the guide manipulator to be moved to position the needle guide at the target location relative to the patient such that the needle guide is in a fixed position relative to the movable patient cradle.

14. The apparatus of claim 13, wherein the processing circuitry is configured to determine the target location of the needle guide and to cause the guide manipulator to be moved to position the needle guide at the target location relative to the patient based at least in part upon the images received from the imaging system.

15. The apparatus of claim 13, further comprising a skin level sensor adapted to be disposed on a skin surface of the patient and to provide an indication to the processing circuitry whether a correction to a spatial orientation of the needle guide is needed.

16. The apparatus of claim 13, wherein the processing circuitry is configured to determine the insertion point and the target point based at least in part on the images received from the imaging system, and
the processing circuitry is configured to determine the location of the needle guide based at least in part on the insertion point and the target point and a length of a needle to be inserted through the needle guide such that a predetermined portion of the length of the needle can be inserted relative to the needle guide, through the insertion point, and into the target point.

17. The apparatus of claim 13, wherein the processing circuitry is configured to determine the insertion point and the target point based at least in part on the images received from the imaging system, and
the processing circuitry is configured to determine the target location to position the needle guide at least in part based on the insertion point and the target point and coordinates derived from the position of the support base with respect to the imaging system.

18. The apparatus of claim 13, wherein the processing circuitry is configured to determine the target location and to position the needle guide at the target location such that the needle guide is in a fixed position relative to the patient and such that a needle can be inserted through the needle guide and moved relative to the needle guide.

19. An apparatus, comprising:
a support base, the support base including a plurality of wheels, the plurality of wheels configured to support the support base and to allow the support base to be moveable to and from a desired position relative to an imaging system, the support base configured to be locked at the desired position;

a guide manipulator supported on the support base and configured to position a needle guide at a target location with respect to a patient disposed on a movable patient cradle of the imaging system, the target location being outside of an imaging space of the imaging system, the needle guide configured to provide a guide to insert a needle through an insertion point on the patient and into a target point within the patient when the patient is disposed on the movable patient cradle; and processing circuitry configured to:
receive images of the patient from the imaging system;
determine, based at least in part on the received images, a location of the insertion point relative to a gantry of the imaging system when the patient is disposed on the movable cradle and the movable cradle is disposed outside of the imaging space of the imaging system such that the insertion point is outside of the imaging space;
determine a directional vector between the insertion point and the target point;
determine the target location of the needle guide to be in line with the directional vector based at least in part on the determined location of the insertion point and the directional vector; and
cause the guide manipulator to be moved to position the needle guide at the target location.

20. The apparatus of claim 19, wherein the support base is selectively lockable to a docking system.

21. The apparatus of claim 19, further comprising a skin level sensor adapted to be disposed on a skin surface of the patient and to provide signals to the processing circuitry indicating whether a correction of a spatial orientation of the needle guide is needed.

22. The apparatus of claim 19, wherein the processing circuitry is configured to determine the target location of the needle guide based at least in part upon the images received from the imaging system.

23. The apparatus of claim 19, wherein the processing circuitry is configured to determine the insertion point and the target point based at least in part on the images received from the imaging system and to determine the target location of the needle guide based at least in part on the insertion point and the target point and coordinates derived from the desired position of the support base relative to the imaging system.

24. The apparatus of claim 19, wherein the processing circuitry is configured to determine the insertion point and the target point based at least in part on the images received from the imaging system and to determine the target location of the needle guide based at least in part on the insertion point and the target point and a length of a needle to be inserted through the needle guide such that a predetermined portion of the length of the needle can be inserted relative to the needle guide, through the insertion point, and into the target point.

25. The apparatus of claim 19, wherein the processing circuitry is configured to determine the target location of the needle guide based at least in part on a length of a needle to be inserted through the needle guide and through the insertion point such that a predetermined portion of the needle can be inserted through the insertion point and into the target point.

26. The apparatus of claim 19, wherein the processing circuitry is configured to determine the target location and to position the needle guide at the target location such that the needle guide is in a fixed position relative to the patient and such that a needle can be inserted through the needle guide and moved relative to the needle guide.

* * * * *